United States Patent [19]

Alexandratos

[11] Patent Number: 5,442,085

[45] Date of Patent: * Aug. 15, 1995

[54] SYNTHESIS OF TETRAALKYL VINYLIDENE DIPHOSPHONATE MONOMER

[75] Inventor: Spiro D. Alexandratos, Knoxville, Tenn.

[73] Assignee: The University of Tennessee Research Corporation, Knoxville, Tenn.

[*] Notice: The portion of the term of this patent subsequent to Oct. 26, 2010 has been disclaimed.

[21] Appl. No.: 131,904

[22] Filed: Oct. 5, 1993

Related U.S. Application Data

[63] Continuation of Ser. No. 985,974, Dec. 4, 1992, Pat. No. 5,256,808.

[51] Int. Cl.$^6$ .............................................. C07F 9/40
[52] U.S. Cl. .................................. 558/142; 558/161
[58] Field of Search ................................ 558/142, 161

[56] References Cited

U.S. PATENT DOCUMENTS 3,686,290  8/1972  Carroll .
4,939,284  7/1990  Degenhardt .

FOREIGN PATENT DOCUMENTS 1204967  5/1967  United Kingdom .

OTHER PUBLICATIONS

Charles R. Degenhardt & Don C. Burdsall, "Synthesis of Ethenylidenebis (phosphonic acid) and Its Tetraalkyl Esters," *J. Org. Chem.* 51, pp. 3488–3490 (1986).
Lehnert W., *Tetrahedron*, 30, pp. 301–305 (1974).

*Primary Examiner*—Robert W. Ramsuer
*Assistant Examiner*—Michael G. Ambrose
*Attorney, Agent, or Firm*—Marshall, O'Toole, Gerstein, Murray & Borun

[57] ABSTRACT

A method of making a monomer of tetraalkyl vinylidene-1, 1-diphosphonate. The monomer is manufactured by combining an aqueous secondary amine solution with a formaldehyde and a tetra (alkyl) methylene diphosphonate. The resulting mixture is maintained at a pH above about 6 and refluxed for two hours to enable reaction to produce the monomer of tetraalkyl vinylidene-1, 1-diphosphonate. The product monomer is then purified to produce the final end product.

20 Claims, 2 Drawing Sheets

SYNTHESIS OF TETRAALKYL VINYLIDENE DIPHOSPHONATE MONOMER

CROSS-REFERENCE TO RELATED APPLICATION

This is a continuation of U.S. application Ser. No. 07/985,974, filed Dec. 4,1992, now U.S. Pat. No. 5,256,808.

The present invention is directed generally to a method of preparing a monomer of tetraalkyl vinylidene-1, 1-diphosphonate. More particuarly, the invention is directed to a method of preparing in a few hours of reaction time the monomer of tetraalkyl vinylidene-1, 1-diphosphonate.

The monomer of tetraalkyl vinylidene-1, 1-diphosphonate has a number of important uses including the manufacture of ion exchange resins, polymeric flame retardants and pharmaceutical applications. Conventional methods of producing this monomer have included (1) thermal dehydration of tetrasodium (1-hydroxyethylidene) bis (phosphonate) at high temperatures and (2) a two-step process as set forth in U.S. Pat. No. 4,939,284 involving the base catalyzed reaction of a methylenebis (phosphonate) ester with a paraformaldehyde followed by addition of an acid catalyst to catalyze elimination of alcohol from the reaction product. The first method, however, has the disadvantage of retiring precise temperature control during the dehydration step and a lengthy, time-consuming purification process. The second method avoids these problems, but the reaction time typically requires ten days to go to seventy percent completion for the tetraisopropyl ester form. In addition, this procedure requires use of an alcohol solvent which complicates processing conditions.

It is therefore an object of the invention to provide an improved method of making a monomer of tetraalkyl vinylidene-1, 1-diphosphonate.

It is another object of the invention to provide a novel method of rapidly forming a monomer of tetraalkyl vinylidene-1, 1-diphosphonate.

It is a further object of the invention to provide an improved method of forming a tetraalkyl vinylidene-1, 1-diphosphonate using an aqueous solvent.

It is yet another object of the invention to provide a novel method of producing a tetraalkyl vinylidene-1, 1-diphosphonate by simultaneously reacting an aqueous solution of formaldehyde with all other aqueous soluble components.

It is still an additional object of the invention to provide an improved method of producing tetraalkyl vinylidene-1, 1-diphosphonate without need for a separate elimination step for intermediates or use of an acid catalyst.

Other objects and advantages of the invention, together with the manner of operation, will become apparent upon reference to the following Detailed Description, Examples and appended claim along with the drawing described below:

DETAILED DESCRIPTION OF A PREFERRED EMBODIMENT

Figure 1:
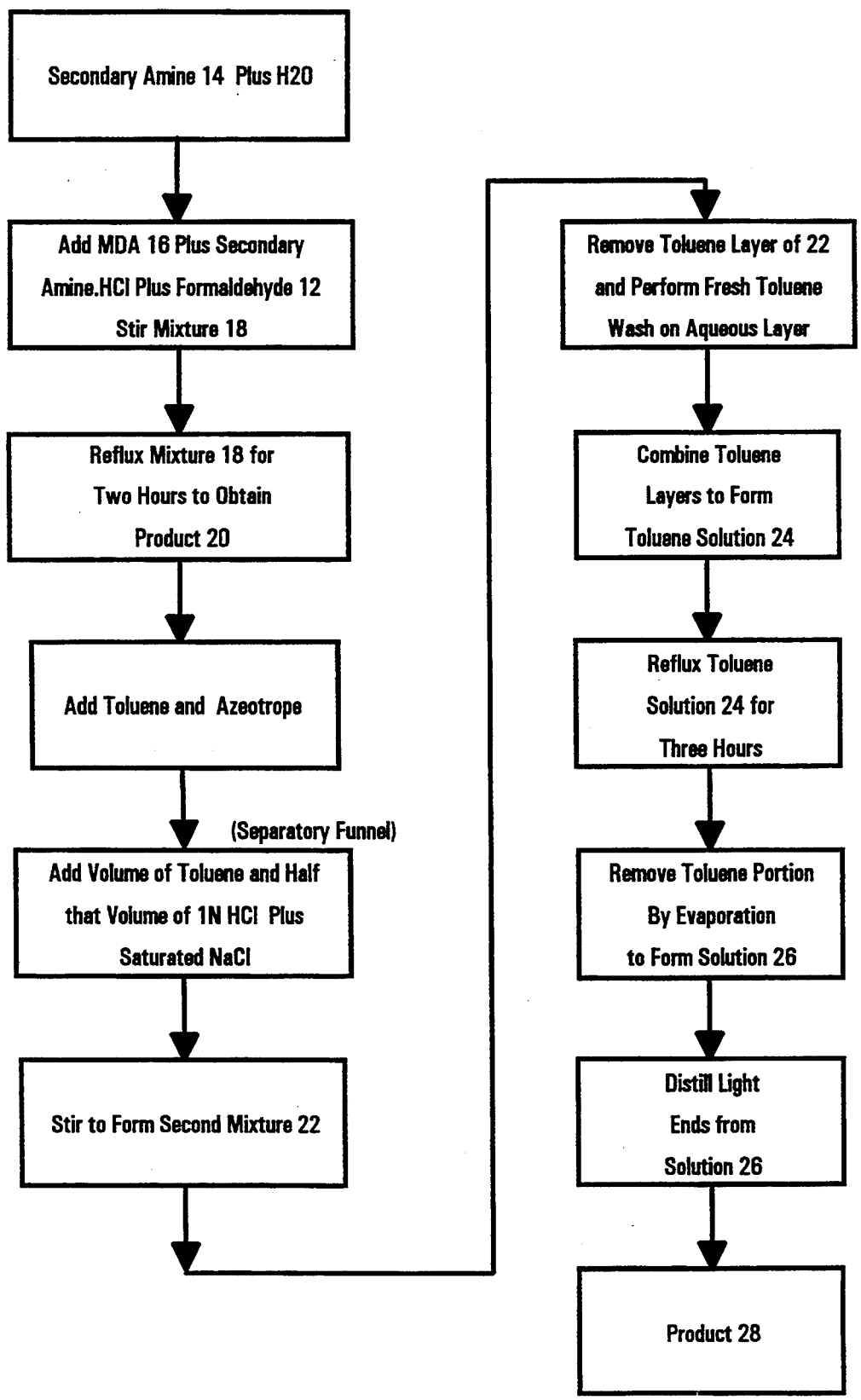
FIG. 1 illustrates as a flow diagram one method of the invention.

A preferred method of manufacturing a monomer of tetraalkyl vinylidene-1, 1-diphosphonate in accordance with the invention is illustrated in FIG. 1. Reactants 10 are accumulated from conventional supply sources, and the reactants 10 include a first reactant 12 of formaldehyde, such as, for example, formalin, paraformaldehyde or trioxane. A second reactant 14 includes a secondary amine, such as, for example, a dipropylamine, dimethylamine or diethylamine. A third reactant 16 includes a tetra (alkyl) methylene diphosphonate (MDA), such as, for example, tetra (methyl), or (ethyl), or (propyl) or (isopropyl) methylene diphosphonate.

In this embodiment the reactants 10 are combined by dissolving the amine into water, the MDA and formalin is added and a resulting mixture 18 is stirred. The pH is monitored to initilize the pH above about 6 in order to allow the reaction to proceed (during which pH will vary in accordance with the reaction). While a most preferred initial pH range is 7.35–7.4, any pH above 6 (and up to 14) will suffice. To control initial pH one can add a secondary amine.HCl, (or other such conventional acidic formulations) with the formalin. Thus, one can add formalin, diethylamine and diethylamine.HCl and MDA. The preferred ratio of formalin to diethylamine and diethylamine HCl to MDA is about 3.2:0.6:1:1. This can be compared to the preferred basic constituent ratios of formalin:dipropylamine:MDA of about 3.2:1.8:1.

The aqueous mixture 18 is placed into a container, such as a heavy walled flask, and closed with a stopper. The mixture 18 is refluxed for about one to two hours to achieve a product 20. Under these most preferred conditions, increased reflux time beyond about two hours does not substantially affect the yield.

In a most preferred form of the invention, a higher purity product can be obtained by purifying the product 20. The product 20 is placed in a separatory funnel. In this preferred method after refluxing the mixture 18 for about one to two hours, but before adding toluene to form the second mixture 22, a toluene and azeotrope is added to the product 20. A volume of toluene and half the toluene volume of 1N HCl (and also preferably including NaCl) is then added to form the second mixture 22. This second mixture 22 is stirred, and the contents are allowed to settle.

The toluene layer of the second mixture 22 is removed, and a fresh toluene wash is performed on the aqueous layer. The two toluene layers are then combined to form toluene solution 24. The combined toluene solution 24 is added to a one-neck flask, and a Dean-Stark trap and condenser are added to the flask. The toluene solution 24 is refluxed for about three hours, emptying the Dean-Stark trap enough (usually several times) until only toluene is being distilled over. The toluene portion is then removed by using a rotary evaporator by heating the toluene solution 24 to 60° C.

The light end products are then distilled off a remaining solution 26 under vacuum conditions (0.05–0.10 torr). Distillation is then stopped when the temperature reaches 104° C. (typically requiring about an hour of time). The flask is then opened to the atmosphere when the remaining solution cools to 25° C. A remaining product mix 28 contains monomeric tetraalkyl vinylidene-1, 1-diphosphonate and MDA in the ratio of about 81:19 or greater and with a product yield of about 90%.

Figure 2:
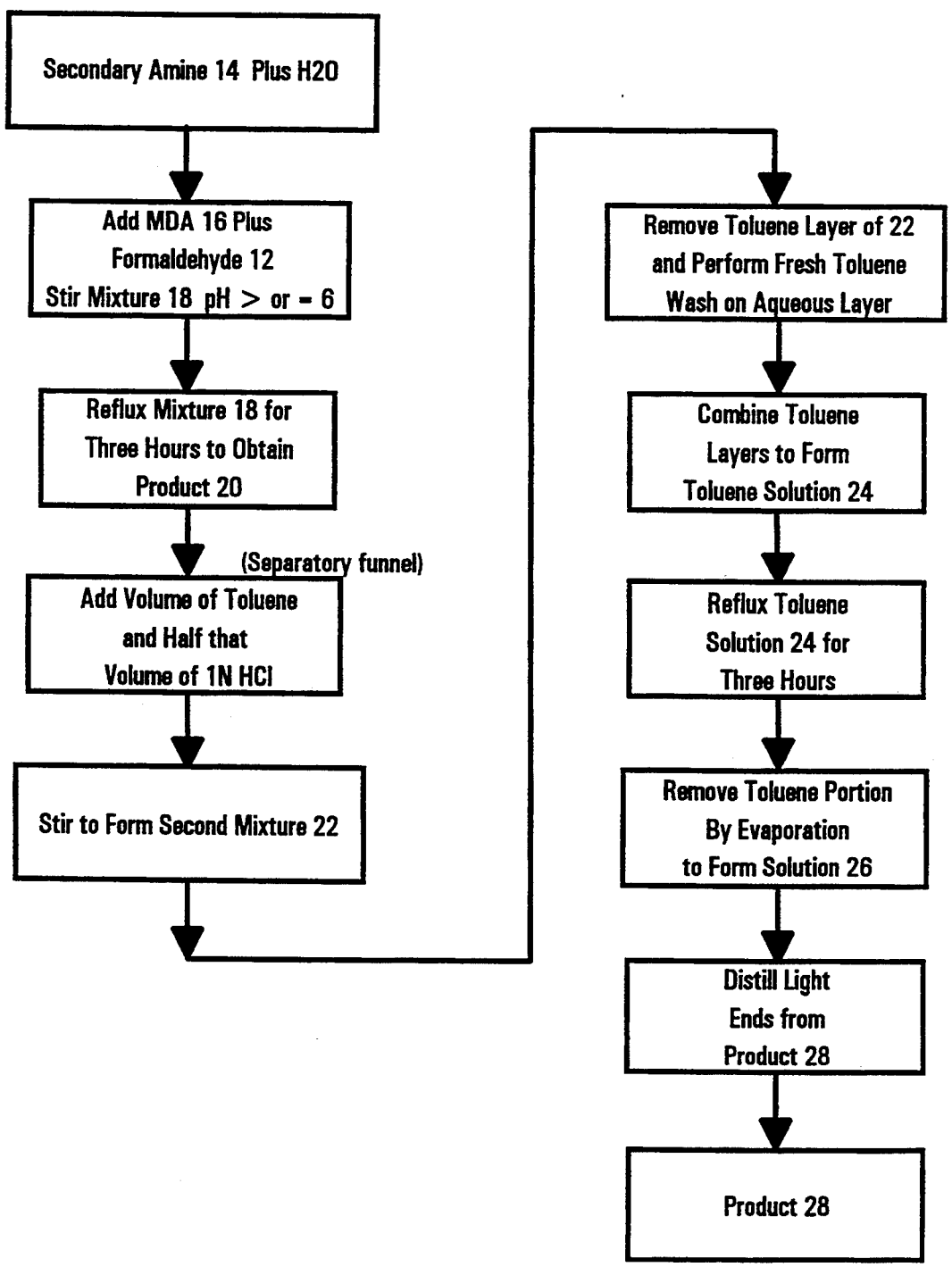
FIG. 2 shows as a flow diagram another method of the invention.

In a second form of the invention, as shown in FIG. 2, the initialized pH in the second step can be achieved by adding a concentrated acid, such as HCl, to establish the pH at or above a value of 6. In the third step the mixture 18 is refluxed for about three hours to achieve the product 20. Extending the reflux time beyond about three hours does not substantially affect the yield.

As in the preferred process of FIG. 1, further purification steps can be used to improve the product purity. As shown in FIG. 2 a volume of toluene and half that volume of 1N HCl is added to the product 20 to form a second mixture 22. Further processing steps are substantially the same as in the process of FIG. 1. The remaining product mix contains monomeric tetraalykyl vinylidene-1, 1-diphosphonate and MDA in the ratio of about 7:3 and greater.

The following nonlimiting examples illustrate several methods of preparation of the tetraalkyl vinylidene-1, 1-diphosphonate.

Example 1

Into a 200 mL heavy-walled flask, place 18.0 g dipropylamine, 13.2 g $H_2O$, and 13.3 mL concentrated HCl. Add the HCl slowly due to the exothermicity of the reaction. Then add 32.1 g tetraisopropyl methylene diphosphonate (MDA) and 25.0 g formalin. Stir and take the pH. Add enough amine (usually 3 mL) to give a final pH of 7.35–7.4. Close the flask with a teflon stopper, reflux for three hours and cool to 25° C.

Place the solution into a separatory funnel, adding 50 mL 1N HCl and 100 mL toluene. Mix, allow to settle and collect the toluene layer. Repeat the wash of the aqueous layer with an additional 100 mL toluene. Combine the toluene layers and reflux for three hours in a flask with an attached condenser and Dean-Stark trap. Cool and remove the toluene with a rotary evaporator. Distill off the light ends under vaccuum (0.05–0.10 torr), and stop the distillation once the temperature is at 104° C. (one hour). Cool the product. Twenty-two grams are isolated in 97% purity with a vinylidene:MDA ratio of 70:30.

Example 2

As in Example 1 above, except the pH is adjusted to 6.85; a resulting vinylidene:MDA ratio is 22.7:72.3.

Example 3

As in Example 1 above, except with no added HCl (pH=14); get vinylidene:MDA ratio is 63.6:36.4. This was repeated for pH values between 8 and 14 in increments of about 1.0. The vinylidene:MDA ratio steadily improved upon reduction below pH of 14 until reaching pH's of 6–7 as shown in other examples.

Example 4

As in Example 1, except use 40% aqueous dimethylamine solution, a 5:2:1 formalin:amine:MDA initial ratio, and a pH of 6.86; a resulting vinylidene:MDA ratio is 3.4:96.6.

Example 5

As in Example 4, except with pH adjusted to 7.21; a resulting vinylidene:MDA ratio is 48.6:51.4.

Example 6

As in Example 4, except with pH of 7.43; a resulting vinylidene:MDA ratio is 56.3:43.7.

Example 7

As in Example 4, except with pH of 7.73; a resulting vinylidene:MDA ratio is 67.4:32.6.

Example 8

As in Example 1, except with paraformaldehyde:diethylamine:MDA in a 5:2:1 ratio and no water as solvent; a vinylidene:MDA ratio of 54.2:45.8 and a 57% yield.

Example 9

As in Example 8, except with a 2:2:1 ratio and a 16.5 hour reaction time; get vinylidene:MDA ratio of 40:60 and 42% yield.

Example 10

The same steps as Example 1 were carried out except a secondary amine complexed with HCl was added along with the formalin making unnecessary the control of pH using HCl in step two of FIG. 1. The ratio of formalin to diethylamine to diethylamine HCl to MDA is preferably about 3.2 to 0.6 to 1 to 1. The diethylamine can be any quantity from 0.1 to 1.0 moles, most preferably 0.6 moles. For 0.4 moles, the yield is 90.3% (MDA/monomer=33/67); for 0.5 moles, the yield is 85.3% (MDA/monomer=25/75); for 0.9 moles, the yield is 54% (MDA/monomer=38/62).

Example 11

The same procedure as Example 10 was followed except the quantity of diethylamine.HCl was varied from 0.1–5.0 moles, the most preferred being 1.0 moles. At 0.6 moles, the yield is 79.8% with MDA/monomer=20/80. At 0.8 moles, the yield is 83.1% with MDA/monomer=20/80.

Example 12

The same procedure as Example 10 was followed except for the quantity of formalin used was varied from 1.0—10.0 moles (most preferably is 3.2 moles). At 4.0 moles the yield is 82.5% with the MDA/monomer=21/79. At 5.0 moles, the yield is 80.6% with the MDA/monomer=23/77.

Example 13

The same procedure as Example 10 was followed, but all quantities of components were increased by the same molar percentage except for the MDA. The product results are substantially insensitive. If increase quantities by 10%, the yield is 84.2% with MDA/monomer-22/78. If quantities are increased by 40%, then the yield is 76% with an MDA/monomer ratio of 19/81.

Example 14

The same procedure as in Example 10 was followed except a variety of secondary amines and secondary amine salts were used. Dipropylamine (0.1–1.0 moles) was combined with dimethylamine.HCl in the ratio of, for example, dipropylamine at 0.6 moles and dimethylamine.HCl at 1 mole. This yields 83.9% with the ratio of MDA/monomer (VDPA) being 34/66.

For diethylamine (0.1–1.0 moles) was combined with dimethylamine.HCl in the preferred ratio of diethylamine at 0.6 moles to dimethylamine.HCl at 1 moles. This yields 86.7% with an MDA/VDPA monomer ratio of 25/75.

For dibutylamine (0.1–1.0 moles) was combined with dimethylamine.HCl in the ratio of 0.6 to 1.0, yielding 58% product. The MDA/VDPA monomer ratio is 33/67.

Example 15

The same procedure as in Example 10 was followed with the effect of temperature on yield and MDA/monomer (VDPA) evaluated. The ratio of formalin to diethylamine to dimethylamine.HCl to MDA was 3.2 to 0.7 to 1.0 to 1.0. For two hours at reflux temperatures the yield was 80.1% with a ratio of 24/76 for MDA/monomer. For two hours at 64° C. the yield was 78.2% with a ratio of 43/57 for MDA/monomer. For two hours at 50° C. the yield was 87.9% with a ratio of 67/23 for the MDA/monomer.

Example 16

A most preferred form of the first embodiment of the invention was prepared as follows:

A. Reactant Charge Was Prepared
1. Obtain a 2 liter reaction vessel with stirrer;
2. Add 34.4 grams (0.314 moles) of diethylamine hydrochloride to the vessel;
3. Add 81.5 grams (75 ml, 1.00 moles) of formalin and stir until diethylamine hydrochloride is completely dissolved;
4. Add 108 grams (102 ml, 0.314 moles) of MDA and stir several minutes until gradient disappears;
5. Add 13.8 grams (20 ml, 0.19 moles) of diethylamine. (The temperature usually rises to 35° C. from 25° C. after the diethylamine is completely mixed).

Be Reflux Mixture
1. Seal the vessel using a suitable accumulator to allow for a volume increase as temperature increases and heat the mixture under reflux @ 100° C. for 2 hours while stirring; and
2. Cool the vessel to room temperature (if handling before next step is necessary).

C. Azeotrope Mixture Preparation
1. Add 628 ml of toluene. The mixture shows two separate phases. The top layer, toluene, is clear and the bottom layer, aqueous, is yellowish-brown;
2. Connect a Dean-Stark trap (or equivalent) to collect water, toluene and coarse contaminant;
3. Stir and rapidly heat the system (begins around 90° C. and then slowly rises to 112° C. when water is completely removed) to reflux azeotrope water with toluene from the mixture. The azeotroped solution which has been treated shows two phases (the lower layer is water and the upper layer is toluene) collected in the trap. Continue heating until water ceases to distill over. The total volume of water collected should be approximately 62.8 ml;
4. Discard the water collected along with residual toluene floating in the trap; and
5. A yellowish-brown residue is present on the bottom of the product flask. Cool the material while agitating to suspend and disperse this residue while it is solidifying.

Purification Steps:

A. Extraction of Product
1. Transfer the above product to a suitable size separatory funnel, and then add 157 ml of NaCl saturated 1N HCl$_{(aq)}$ solution*.

* 200 ml of 1 N HCl$_{(aq)}$+50 g of NaCl. The mixture is stirred until NaCl is completely dissolved before using.

2. Agitate the system vigorously until fully mixed, and then allow system to settle until upper toluene layer becomes clear (usually takes 5-10 minutes).
3. Drain and collect lower layer (contains aqueous phase and some solids) from the bottom;
4. The toluene phase remaining in the separatory funnel is collected for further treatment;
5. Pour the aqueous solution and solid mixture obtained from step 3 above back to the separatory funnel and then add 314 ml of fresh toluene. The mixture is treated by the same procedures as purification steps 2, 3 and 4 above; and
6. Discard aqueous phase and solids mixture (the total volume is about 220 ml).

B. Second azeotrope steps
1. The toluene solutions obtained from purification steps A.4 and 5 above are mixed and then azeotroped under reflux (the temperature should be around 110° C.±5° C.) for 3 hours in the same apparatus used before. Discard the first 314 ml of solution collected in the trap (contains mostly toluene and a small amount of water) and then continue to heat the solution at reflux until the three hours have elapsed; and
2. After the system is cooled to 25° C. (room temperature), the solution is filtered and is then ready for vacuum distillation.

C. Vacuum Distillation
1. Distill most of the toluene off under vacuum (10 mmHg) at 70° C. (starts from 50° C. and then rises to 70° C. with a rate of about 1° C./min) for 1 hour;
2. Distill the remaining toluene and impurities off under high vacuum (0.1 mmHg) at 105° C. for 30 minutes*; and

* Note that other vacuum experiments show that a yield ratio of monomer to tetra (alkyl) methylene diphosphonate is up to about 9:1 for very high vacuum processing.

3. Turn off the heat and allow the system to cool to room temperature. For safety purposes, do not release vacuum until the product is fully cooled.

Ninety-six grams (89.8% yield) of monomer solution in a MDA:VDPA and a ratio of 19/81 is obtained through this above described procedure.

What is claimed is:

1. A method of making a tetraalkyl vinylidene-1, 1-diphosphonate, comprising the steps of:
   (a) combining a secondary amine, a formaldehyde and a tetra (alkyl) methylene diphosphonate to form a reaction mixture, wherein said tetra (alkyl) methylene diphosphonate comprises tetra (methyl) methylene diphosphonate, tetra (ethyl) methylene diphosphonate, tetra (propyl) methylene diphosphonate, tetra (isopropyl) methylene diphosphonate, and mixtures thereof;
   (b) adjusting the pH of said reaction mixture above about 6; and
   (c) heating said reaction mixture of step (b) for a sufficient time at a temperature of 50° C. to 100° C. for components of the reaction mixture to react and provide a reaction product comprising the tetraalkyl vinylidene-1, 1-diphosphonate.

2. The method of claim 1 wherein said secondary amine comprises dipropylamine, dibutylamine, diethylamine, dimethylamine, higher order amines, or mixtures thereof.

3. The method of claim 1 wherein said formaldehyde comprises formalin, a paraformaldehyde, trioxane, or mixtures thereof.

4. The method of claim 1 wherein the pH is adjusted to about 7 to about 8 in step (b).

5. The method of claim 1 wherein the reaction is performed in about two hours time.

6. The method of claim 1 further including a step of purifying said reaction product of step (c).

7. The method of claim 6 wherein said purification step comprises:
   (1) adding toluene and an acid to said reaction product of step (c) to form a diluted reaction product; and
   (2) heating said diluted reaction product to a sufficient temperature to evaporate and distill unwanted portions of said diluted reaction product to provide a purified tetraalkyl vinylidene-1, 1-diphosphonate.

8. The method of claim 7 wherein the tetraalkyl vinylidene-1, 1-diphosphonate is about 97% pure.

9. The method of claim 7 wherein the tetraalkyl vinylidene-1, 1-diphosphonate has a vinylidene:MDA ratio in the range of about 3.4 to 96.6 to 9 to 1.

10. The method of claim 1 wherein the pH is adjusted to above about 6 to about 14 in step (b).

11. A method of making a tetraalkyl vinylidene-1, 1-diphosphonate, comprising the steps of:
   (a) combining a secondary amine with water to form an aqueous amine solution;
   (b) admixing a formaldehyde and a tetra (alkyl) methylene diphosphonate with the aqueous amine solution to form an aqueous reaction solution, wherein said tetra (alkyl) methylene diphosphonate comprises tetra (methyl) methylene diphosphonate, tetra (ethyl) methylene diphosphonate, tetra (propyl) methylene diphosphonate, tetra (isopropyl) methylene diphosphonate, and mixtures thereof;
   (c) adjusting pH of the aqueous reaction solution to between about 6 and 14;
   (d) heating the aqueous reaction solution at a temperature of 50° C. to 100° C. for a sufficient time to form the tetraalkyl vinylidene-1, 1-diphosphonate; and
   (e) purifying the tetraalkyl vinylidene-1, 1-diphosphonate.

12. The method of claim 11 wherein the pH is adjusted to about 6.85 to about 7.75 in step (c).

13. The method of claim 11 wherein the formaldehyde comprises formalin, paraformaldehyde, trioxane, or mixtures thereof.

14. The method of claim 11 wherein the secondary amine comprises dipropylamine, diethylamine and dimethylamine, higher order amines, or mixtures thereof.

15. The method of claim 11 wherein the ratio range of said tetraalkyl vinylidene-1, 1-diphosphonate to said tetra (alkyl) methylene diphosphonate is from about 3.4 to 96.6 to about 9 to 1.

16. The method of claim 11 wherein the ratio of said tetraalkyl vinylidene-1, 1-diphosphonate to said tetra (alkyl) methylene diphosphonate is about 9 to 1.

17. A method of making tetraalkyl vinylidene-1, 1-diphosphonate, comprising the steps of:
   (a) combining a secondary amine, a formalin and a tetra (alkyl) methylene diphosphonate to form a reaction mixture, wherein said tetra (alkyl) methylene diphosphonate comprises tetra (methyl) methylene diphosphonate, tetra (ethyl) methylene diphosphonate, tetra (propyl) methylene diphosphonate, tetra (isopropyl) methylene diphosphonate, and mixtures thereof; and
   (b) heating said reaction mixture at a temperature of 50° C. to 100° C. for a sufficient time to obtain a reaction product comprising the tetraalkyl vinylidene-1, 1-diphosphonate.

18. The method of claim 17 wherein the secondary amine comprises a secondary amine hydrochloride.

19. The method of claim 17 wherein the secondary amine is present in an amount of about 0.1 to about 1 mole.

20. The method of claim 17 wherein said formalin is present in an amount of about 0.1 to about 1 mole.

* * * * *

UNITED STATES PATENT AND TRADEMARK OFFICE
CERTIFICATE OF CORRECTION

PATENT NO. : 5,442,085
DATED : August 15, 1995
INVENTORS : SPIRO D. ALEXANDRATOS It is certified that error appears in the above-identified patent and that said Letters Patent is hereby corrected as shown below:

Column 1, line 13, "More particuarly," should be --More particularly,--.

Column 1, line 31, "retiring" should be --requiring--.

Column 2, line 19, "initilize" should be --initialize--.

Column 3, line 37, "vaccuum" should be --vacuum--.

Column 5, line 32, "Be Reflux Mixture" should be --B. Reflux Mixture--.

Signed and Sealed this

Twentieth Day of February, 1996

Attest:

Attesting Officer

BRUCE LEHMAN

Commissioner of Patents and Trademarks